United States Patent
Thiele et al.

(10) Patent No.: US 8,805,036 B2
(45) Date of Patent: Aug. 12, 2014

(54) IMAGE BASED CLINICAL TRIAL ASSESSMENT

(75) Inventors: Frank O. Thiele, Seattle, WA (US); Satoshi Minoshima, Seattle, WA (US)

(73) Assignee: Koninklijke Philips N.V., Eindhoven (NL)

(*) Notice: Subject to any disclaimer, the term of this patent is extended or adjusted under 35 U.S.C. 154(b) by 402 days.

(21) Appl. No.: 13/144,172

(22) PCT Filed: Dec. 9, 2009

(86) PCT No.: PCT/IB2009/055614
§ 371 (c)(1),
(2), (4) Date: Jul. 12, 2011

(87) PCT Pub. No.: WO2010/082096
PCT Pub. Date: Jul. 22, 2010

(65) Prior Publication Data
US 2011/0263949 A1    Oct. 27, 2011

Related U.S. Application Data

(60) Provisional application No. 61/144,231, filed on Jan. 13, 2009.

(51) Int. Cl.
*G06K 9/00*    (2006.01)

(52) U.S. Cl.
USPC .......................................... 382/128; 128/922

(58) Field of Classification Search
CPC ... G06T 7/0012; G06T 11/003; G06T 3/0068; G06T 7/0016; G06T 7/0024; A61B 6/481; A61B 6/5211; A61B 6/5294; A61B 5/4848; A61B 5/742; G06F 19/3437; G06F 19/12
USPC .......... 382/100, 128, 129, 130, 131, 132, 294; 128/922; 378/4–27
See application file for complete search history.

(56) References Cited

U.S. PATENT DOCUMENTS

| | | | | |
|---|---|---|---|---|
| 6,556,695 | B1* | 4/2003 | Packer et al. | 382/128 |
| 6,751,290 | B2* | 6/2004 | Salb | 378/98.9 |
| 7,043,415 | B1* | 5/2006 | Dunlavey et al. | 703/12 |
| 7,747,308 | B2* | 6/2010 | Hundley et al. | 600/414 |
| 7,907,759 | B2* | 3/2011 | Hundley et al. | 382/128 |
| 8,103,073 | B2* | 1/2012 | Hundley et al. | 382/128 |

(Continued)

OTHER PUBLICATIONS

Kaneta, T., et al.; Dementia clinical trials with longitudinal FDG PET: Improved statistical power using intra-subject registration; 2009; J. of Nuclear Medicine, Society of Nuclear Medicine; 50(suppl):26.

(Continued)

*Primary Examiner* — Anand Bhatnagar

(57) ABSTRACT

A method for assessing a treatment in a trial includes obtaining images generated from image data acquired at different times during a trial time period for a same region of interest of a subject. The treatment is administered to the subject for the trial. The method further includes co-registering the images and mapping the co-registered images to a reference image representing the region of interest. The method further includes generating a trial image of the region of interest showing at least one of structural or functional physiological changes that occurred during the trial time period based on the mapped co-registered images, and displaying the trial image.

30 Claims, 3 Drawing Sheets

(56) References Cited

U.S. PATENT DOCUMENTS

| | | |
|---|---|---|
| 2005/0031210 A1 | 2/2005 | Shen et al. |
| 2005/0141757 A1* | 6/2005 | Ayache et al. ............... 382/128 |
| 2007/0230757 A1* | 10/2007 | Trachtenberg et al. ....... 382/128 |

OTHER PUBLICATIONS

Leung, K. K., et al.; Automatic Quantification of Changes in Bone in Serial MR Images of Joints; 2006; IEEE Trans. on Medical Imaging; 25(12)1617-1626.

Lorenzo-Valdes, M., et al.; Atlas-Based Segmentation and Tracking of 3D Cardiac MR Images Using Non-rigid Registration; 2002; Lecture Notes in Computer Science (Proc. Medical Image Computing and Computer-Assisted Intervention) vol. 2488; pp. 642-650.

Rey, D., et al.; A Spatio-temporal Model-based Statistical Approach to Detect Evolving Multiple Sclerosis Lesions; 2001; Mathematical Methods in Biomedical Image Analysis; pp. 105-112.

Zijdenbos, A. P., et al.; Automatic "Pipeline" Analysis of 3-D MRI Data for Clinical Trials: Application to Multiple Sclerosis; 2002; IEEE Trans. on Medical Imaging; 21(10)1280-1291.

* cited by examiner

IMAGE BASED CLINICAL TRIAL ASSESSMENT

CROSS REFERENCE TO RELATED APPLICATIONS

This application claims the benefit of U.S. provisional application Ser No. 61/144,231 filed Jan. 13, 2009, which is incorporated herein by reference.

The following generally relates to assessing clinical trials using medical imaging data.

Clinical trials in healthcare provide information that is used to determine the clinical efficacy of a new drug or device. A typical drug trial involves several subjects, some of which ingest the drug under trial and others of which ingest a placebo. The subjects are monitored over time for physiological changes, which are hypothesized, in response to the drug. The change resulting from the drug or the degree of change between the two groups of subjects is analyzed and used to test the hypothesis and determine the efficacy of the new drug.

Medical imaging can be used to monitor structural and/or functional changes in the subject in response to the drug. By way of example, longitudinal imaging, which involves acquiring images of the same anatomy for the same subject over time allows for the investigation of the affect of the drug on the subject over time. Quantitative imaging procedures currently serve as surrogate endpoints in clinical trials. A standard procedure for quantitative brain imaging is statistical brain mapping. In statistical brain mapping, the brain image of a subject is statistically compared to a control collective of brain images.

With one technique, a new drug is administered to some subjects and a placebo is administered to other subjects, and the subjects are scanned over time. The resulting images are spatially normalized to standard coordinates, and a statistical analysis is performed on the normalized images. The results can be mapped to a three dimensional model of the brain surface or a surface projected on the model. The statistical analysis may provide t-statistics or a z-score, which is a scalar value per voxel. A final image is rendered showing those voxels that have a statistical value above a given threshold. From such an image, the efficacy of the drug can be determined.

The literature notes that the cost of a clinical trial makes up as much as sixty percent (60%) of the total development cost of a new drug. A relatively high cost component of a trial is the number of subjects enrolled in the trial; more subjects leads to a more expensive trial. Lower variation results in higher statistical power, or a greater ability of the trial to reliably detect the magnitude of the effect of the drug relative to the placebo. Unfortunately, the number of subjects enrolled in a particular trial generally depends on the variability (or noise) of the trial assessment technique, with the number of subjects required for a trial and, thus the cost of the trial, increasing with increased variability.

Aspects of the present application address the above-referenced matters and others.

According to one aspect, a method for assessing a treatment in a trial includes obtaining images generated from image data acquired at different times during a trial time period for a same anatomical region of a subject. The treatment is administered to the subject for the trial. The method further includes co-registering the images and mapping the co-registered images to a reference image representing the scanned anatomical region. The method further includes generating a trial image of the anatomical region showing at least one of structural or functional physiological changes that occurred during the trial time period based on the mapped co-registered images, and displaying the trial image.

In another aspect, a computer implemented method for determining an efficacy of a treatment in a trial includes co-registering images corresponding to a same region of a subject to a baseline image via a single affine registration by way of computer. The images are acquired at different times after administering a trial treatment to the subject. The method further includes applying a computer implemented transformation to the co-registered images to fit the co-registered images to an anatomical model representing the anatomical region under consideration. The method further includes generating a value representing a physiological change in the region of interest based on the mapped co-registered images. The method further includes determining an efficacy of the treatment based on the value.

In another aspect, a system includes a trial population estimator that generates a first signal indicative of an estimated trial population size based on a given statistical power and an image analysis algorithm. The algorithm includes transforming co-registered images of a same region of interest of a subject administered a trial treatment to a model based on a same transformation. The system further includes a trial cost estimator that generates a second signal indicative of an estimated clinical trial cost as a function of the estimated trial population size, and a service that provides the second signal to a client over a computer network.

In another aspect, a system includes a service that generates a signal indicative of a trial image analysis algorithm based on a trial budget and a statistical power, both provided by a client over a network, wherein the algorithm includes transforming co-registered images of a same region of interest of a subject administered a trial treatment to a model based on a same transformation, and the service provides the signal to the client over the network.

Still further aspects of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 illustrates an example clinical trial flow diagram. The illustrated flow diagram provides for increased clinical trial statistical power or reduced clinical trial population for a given statistical power by decreasing clinical trial data variability.

At 102, a treatment for clinical trial such as a new pharmaceutical or device is identified. One or more preliminary experiments can be conducted to gain insight for the planning of the clinical trial. This may include obtaining information about characteristics of suitable subjects for the trial (the trial population), comparative data such as alternative treatments and/or a placebo, clinical trial budgets, etc.

At 104, a treatment hypothesis is determined. The hypothesis may include predicting results, determining a desired outcome, etc.

At 106, a desired statistical power is set for the trial. The statistical power provides a quantitative measure of the ability of the trial to reliably detect the affect of the treatment.

At 108 an image analysis algorithm for the trial is identified based on the statistical power. In one instance, the algorithm includes affinely co-registering images for a subject of the trial and subsequently stereotactictly normalizing each of the co-registered images based on an average image, as described in greater detail below in connection with FIG. 2. In another example, the algorithm includes affinely co-registering images for the subject and subsequently stereotacticly normalizing each of the co-registered images based on a reference, as described in greater detail below in connection with FIG. 3.

Figure 2:
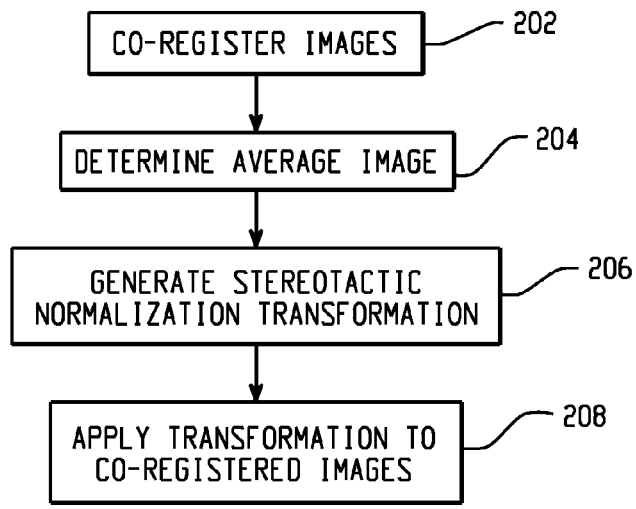
FIG. 2 illustrates a first example image standardization technique.
Figure 3:
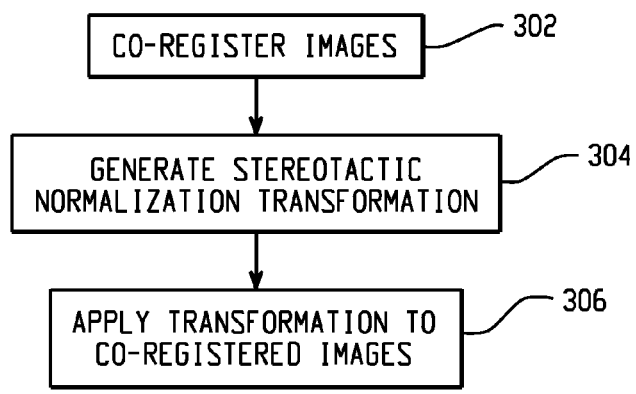
FIG. 3 illustrates a second example image standardization technique.

The approaches of FIGS. 2 and 3 utilize a single estimated non-rigid (elastic) registration transformation to transform affinely co-registered images and can improve the statistical power of a clinical trial for a given trial population size relative to a configuration in which non-aligned (non co-registered) images are individually transformed via different non-rigid (elastic) registrations as the approaches of FIGS. 2 and 3 add relatively less variance to the post-processed images and thus provide relatively higher statistical power for the clinical trial. Alternatively, the trial population size can be reduced for a given statistical power. Individually transforming non co-registered images using different elastic registrations is not as accurate and adds more variation (noise) to the processed images, which decreases statistical power.

At 110, a trial population size is determined based on the statistical power and the analysis algorithm. The size of the population generally increases with increasing variability and thus can be decreased using the algorithms of FIGS. 2 and 3.

At 112, an estimated cost of the trial is determined as a function of the population size.

At 114, it is determined whether the estimated cost is less than a target population cost ($T_{cost}$) of the trial. Alternatively, the estimated cost is added with the other costs of the trial and the aggregated cost is compared with the trial budget.

In this example, if the estimated cost is greater than the target cost, then the trial is not conducted and flow ends at 116, and if the estimated cost is less than the target cost, then the trial proceeds.

At 118, the trial and alternative/control treatments are administered to the subjects. By way of example, the trial treatment can be administered to a first group of the subjects. A placebo can be administered to a second different group of the subjects. Alternatively or additionally, one or more alternative treatments can be administered to one or more other groups.

At 120, the subjects are monitored over time. In one embodiment, this includes acquiring image data through periodically scanning or imaging the subjects over some time during such as hours, days, weeks, months or years. For example, in one instance baseline images for the subjects are acquired before, during or shortly after administration of the trial treatment, alternative treatment and/or placebo.

Post trial treatment, alternative treatment and/or placebo administration image data or images generated therefrom are subsequently obtained over the trial period. The image can be a positron emission tomography (PET), single photon emission computed tomography (SPECT), computed tomography (CT), magnetic resonance (MR), ultrasound (US), other medical and/or non-medical image.

At 122, the resulting images for each subject are standardized in accordance with the image analysis algorithms identified at 108 as described in greater detail below. As noted above, examples of such algorithms are described in connection with FIGS. 2 and 3. The images can be presented for display on a display of a computing device before and/or after standardization.

At 124, the results of the trial are analyzed. In one instance, this includes performing a computer based statistical analysis. The statistical analysis may include determining a physiological (structural and/or functional) change for a region of interest over time for each subject via the standardized images. This includes measuring and recording a value representing a change between the images for each patient over time. The value may include information such a color or gray scale value representing a degree of change.

The value may be presented visually or graphically through one or more images and/or numerically through numeric characters. The identified change may correspond to a particular region of interest selected by a user or otherwise, and may include a single voxel, a plurality of voxels, or the entire image. The displayed image may only show pixels corresponding to changes greater than a threshold value, may highlight or otherwise emphasize pixels corresponding to changes greater than a threshold value, etc.

At 126, the treatment is assessed based on the analyzed results. For example, the results can be used to assess the safety and effectiveness of the new medication or device on a specific kind of patient, of a different dose of a medication than that commonly used, of an already marketed medication or device for a new indication, to determine whether the new medication or device is more effective for a patient's condition than an already used, standard medication or device, etc. For example, if the difference is greater than a hypothesized difference, then the hypothesis is confirmed, and if the difference is less than the hypothesized difference, then the hypothesis is rejected.

Figure 1:
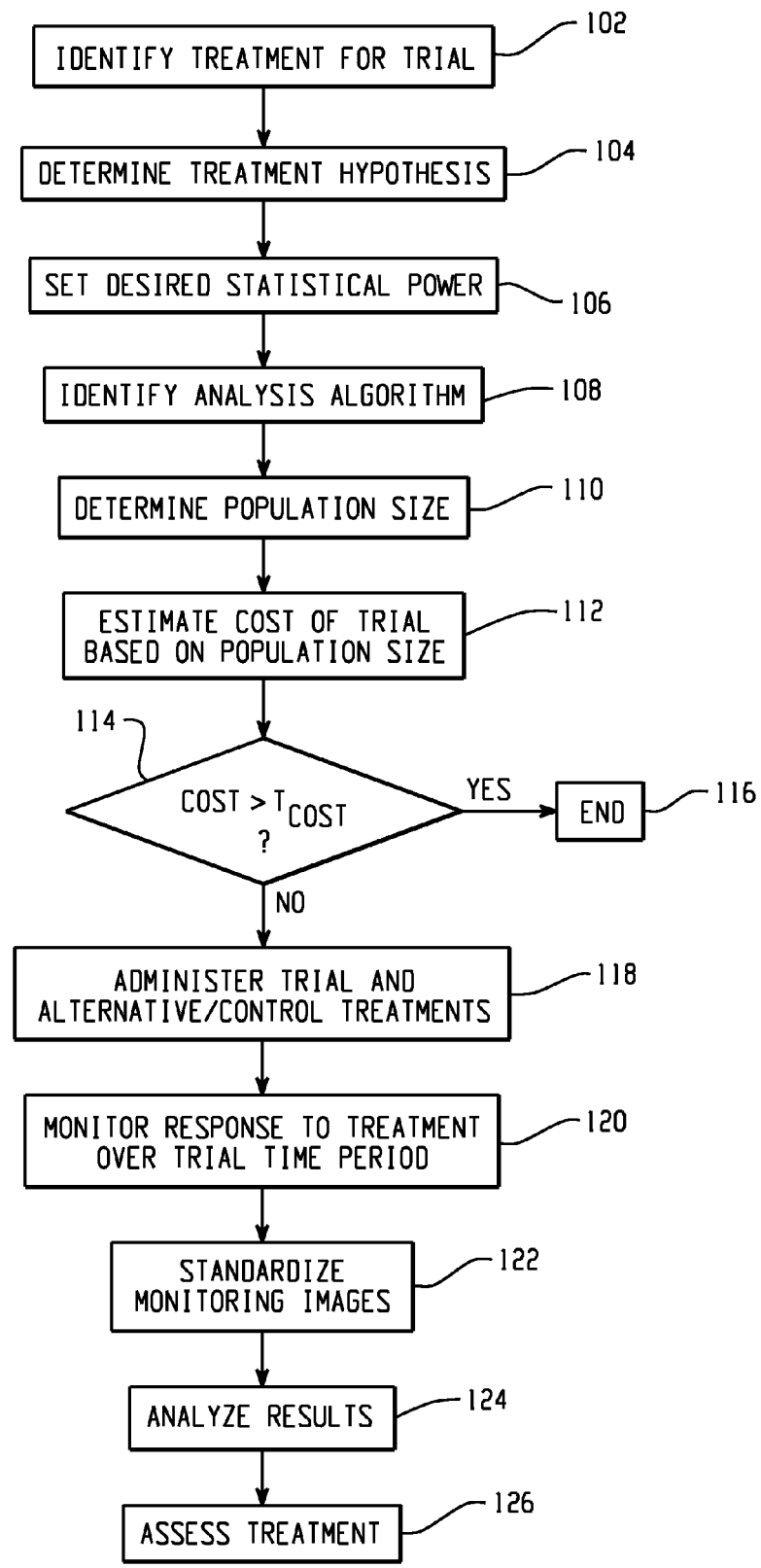
FIG. 1 illustrates an example clinical trial flow diagram.

FIG. 2 illustrates an example image standardization technique that can be employed in connection with act 122 of FIG. 1. The technique includes generating a single estimated elastic transformation based on an average of co-registered images and applying this estimated elastic transformation to each of the co-registered images.

At 202, the images for each subject are co-registered with each other using an affine registration. In one non-limiting instance, this includes identifying one of the images as a reference or baseline image, and the other images are co-registered to the reference image. The references image can be the first image in time, the last image in time, or any image therebetween. The reference image may be manually selected by a user and/or automatically selected via computer executable instructions being executed by a computer processor.

Figure 4:
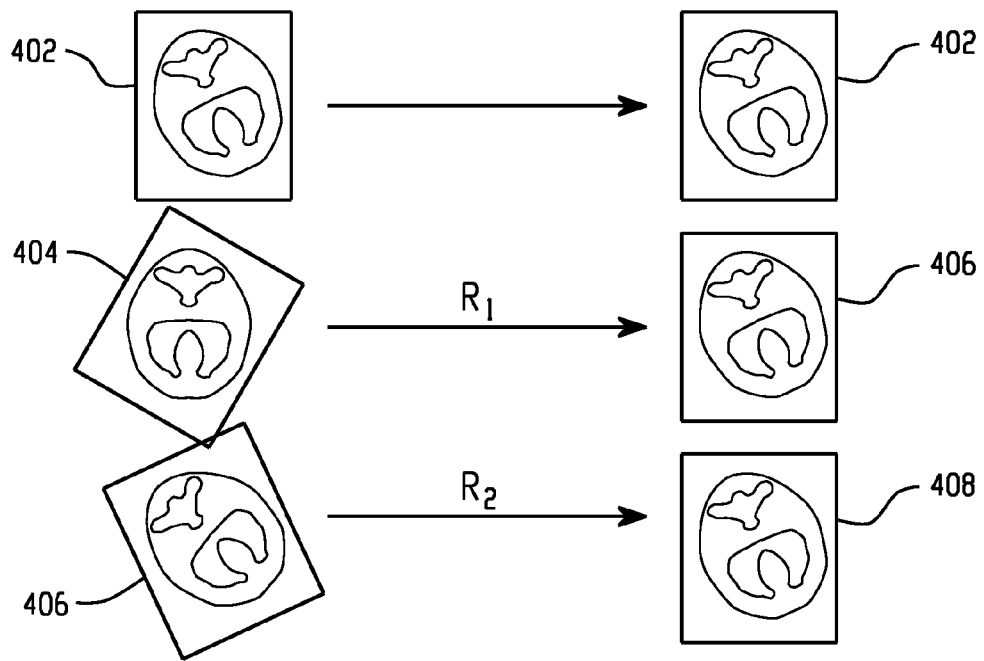
FIG. 4 shows an example of co-registering images for a subject.

Generally, prior to co-registration the images for a subject are not-aligned with respect to each other. During registration, the images are rotated and/or translated and/or geometrically scaled with respect to the reference image so that the anatomy therein is aligned. FIG. 4 shows an example in which a series of three non-aligned images are co-registered. The depicted 2-dimensional image is a representation of a 3-dimensional image. In this example, an image 402 is selected as the reference or baseline image, and images 404 and 406 are registered with the image 402 based on respective registration transformation R1 and R2 to produce co-registered images 402, 406 and 408.

Returning to FIG. 2, at 204 an average image is generated. The average image is an average of the co-registered images and can be generated by summing the co-registered images and dividing the summation by the total number of summed images.

At 206 a stereotactic normalization elastic transformation is generated based on the average image and a model of anatomy of interest. In one instance, the transformation represents a mapping between the average image and an anatomical model of interest. A suitable transformation maps each image pixel to a known anatomical position.

At 208, the elastic transformation is applied to each of the co-registered images. The transformation elastically transforms or warps each of the co-registered images to fit the model.

Figure 5:
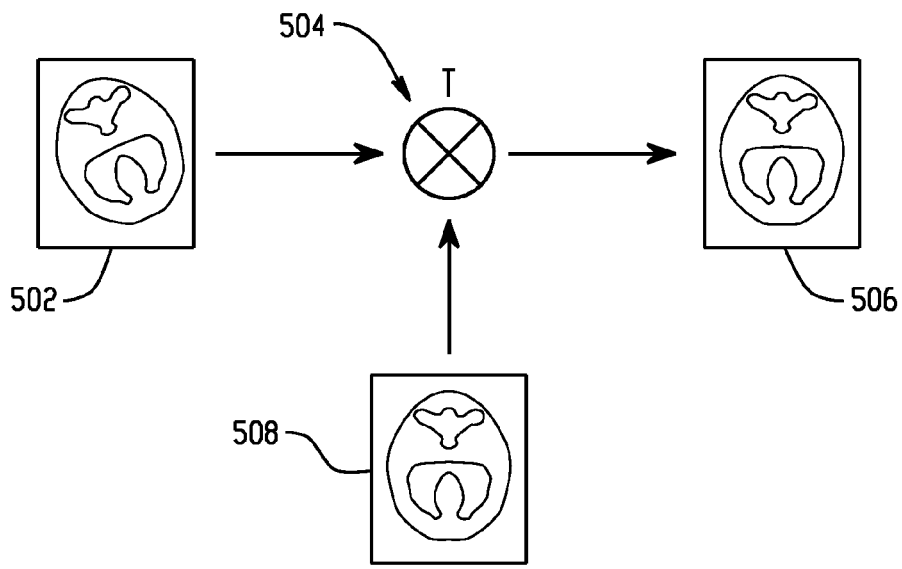
FIG. 5 shows an example of transforming a co-registered image.

FIG. 5 shows an example in which a co-registered image 502 is transformed with a transformation 504 to generate a standardized image 506. In this example, the transformation 504 is based on a template image 508.

The resulting stereotacticaly normalized co-registered images can be analyzed as discussed above in connection with 124.

FIG. 3 illustrates an example image standardization technique that can be employed in connection with act 122 of FIG. 1. The technique includes generating a single estimated elastic transformation based on a reference or baseline co-registered image and applying the estimated elastic transformation to the co-registered images.

At 302, similar to 202, the images for a subject are co-registered with each other using a rigid registration.

At 304, one of the images is used to generate the stereotactic normalization transformation. The image may be the reference image for the co-registration or a different image. As discussed above, the transformation represents a mapping between the image and an anatomical model. Note that if the first image in time is used to generate the transformation, steps 302 and 304 may be exchanged in order, i.e. 304 first, then 302 for each additional image of the same subject.

At 306, each co-registered image is transformed via the same stereotactic normalization transformation. The co-registered images can be transformed in parallel, for example, once all of the images are acquired, or sequentially as images are obtained.

The resulting stereotacticaly normalized co-registered images can be analyzed as discussed above in connection with 124.

The approach of FIG. 2 generally provides higher statistical power relative to the approach of FIG. 3. However, if additional images are acquired for a subject after the elastic transformation is generated, then the transformation is re-calculated to take into account the later acquired images.

As discussed herein, the approaches of FIGS. 2 and 3 may facilitate reducing trial population size and thus trial cost by improving statistical power through reducing variability in measurement. The following provides a non-limiting example. Assume a two-sided significance level ("p-value") of 0.05, a statistical power requirement of 0.8, and a hypothesized effect size of 10% between 2 groups of equal size. Also assume a mean outcome measure of 0.01 (=>delta=0.001), with a standard deviation of 0.014 using the approaches of FIGS. 2 and 3 and a standard deviation of 0.015 using an approach where the images are not co-registered and each image is individually transformed with its own transformation. An approximated population size for the approaches of FIGS. 2 and 3 is 3078, whereas an approximated population size for the other approach is 3533. Hence, using the approaches of FIGS. 2 and 3 would reduce the trial population size relative to the other approach.

Those of ordinary skill in the art will recognize that the various techniques described herein may be implemented by way of computer readable instructions stored on a computer readable storage medium accessible to a computer processor. When executed, the instructions cause the processor(s) to carry out the described techniques. Note that the medium need not be local to the processor; the instructions may be downloaded or otherwise accessed via a communication network such as the internet. The relevant computers may also be located remote from the imaging system, with the scan data transferred via a suitable network or other medium.

Figure 6:
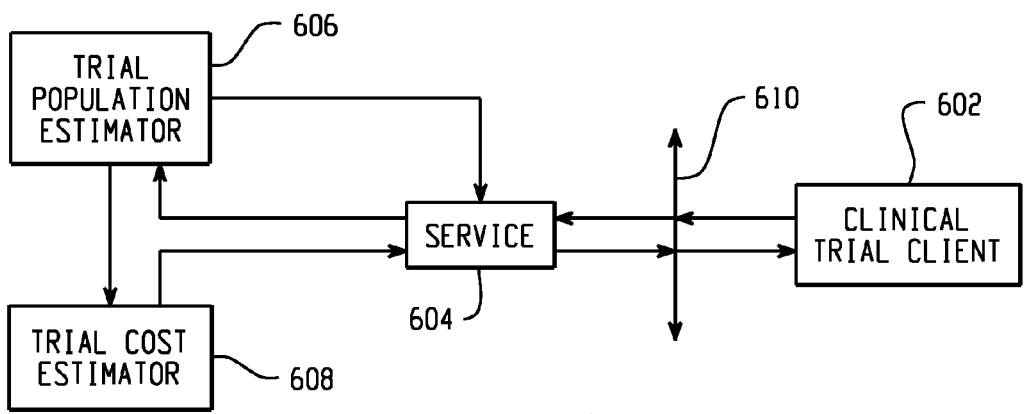
FIG. 6 illustrates a clinical trial planning service.

FIG. 6 illustrates an example clinical trial planning service. As shown, a clinical trial client 602 provides clinical trial information to a service 604, which estimates a cost of the clinical trial based on the clinical trial information. In the illustrated example, the client 602 and the service 604 communicate electronically, via wire or wirelessly, through a computer network 610 such as the Internet, an intranet, etc. The service 604 may be subscription or otherwise based.

The clinical trial client 602 may be a financial or accounting client or other client that may determine or influence whether a clinical trial is conducted or not. In one instance, the clinical trial client 602 provides information such as a desired clinical trial statistical power, an algorithm used to analyze the data, and/or known variations with the algorithm. The algorithm may be a statistical power enhancing algorithm such as those described in connection with FIGS. 1-3 above.

This information is provided to a clinical trial population determiner 606, which estimates the population for the trial based on the desired statistical power, the algorithm used to analyze the data, and/or the known variations. A cost estimator 608 estimates a cost of the trial as a function of trial population. A signal indicative of the cost estimate is provided to the clinical trial client 602 by the service 604. The cost estimate may include alternatives such as a cost estimate for a clinical trial with greater statistical power due to the analysis algorithm and a cost estimate for a clinical trial with a reduced population at the desired statistical power due to the analysis algorithm.

In another embodiment, the clinical trial client 602 provides information such as a desired clinical trial statistical power and a budget allocated for a trial population, and the service 602 determines a suitable algorithm(s) and/or an estimated population size based on the information. The service 604 provides one or more signals indicative of the suitable algorithm(s) and/or the estimated population size to the client 602. In this embodiment, the cost estimator 608 can be omitted.

The invention has been described with reference to various embodiments. Modifications and alterations may occur to others upon reading the detailed description. It is intended that the invention be constructed as including all such modifications and alterations insofar as they come within the scope of the appended claims or the equivalents thereof.

The invention is claimed to be:

1. A method for assessing a treatment under trial, comprising:
   obtaining images generated from image data acquired at different times during a trial time period for a same anatomical region of a subject, wherein the treatment is administered to the subject for the trial;
   co-registering the images;
   mapping the co-registered images to a reference image representing the anatomical region;
   generating a trial image of the anatomical region showing at least one of structural or functional physiological changes that occurred during the trial time period based on the mapped co-registered images; and displaying the trial image.

2. The method of claim 1, further including performing a statistical analysis over the trial image and trial images for one or more other subjects receiving an alternative treatment or a placebo to assess efficacy of the treatment under trial.

3. The method of claim 1, further comprising: selecting one of the images as a baseline image; wherein co-registering the images includes co-registering the images with the selected baseline image.

4. The method of claim 1, further comprising:
generating an average image based on the co-registered images; and
generating a transformation based on the average image; wherein mapping the co-registered images includes transforming the co-registered images with the generated transformation.

5. The method of claim 4, further comprising: generating the transformation based on an anatomical model representing the region of interest.

6. The method of claim 5, wherein the anatomical model is a three dimensional volume.

7. The method of claim 5, wherein the transformation warps the co-registered images to fit the model.

8. The method of claim 1, further comprising:
selecting one of the co-registered images as a reference image; and
generating a transformation based on the reference image; wherein mapping the co-registered images includes transforming the co-registered images with the generated transformation.

9. The method of claim 1, further comprising: performing a computer based statistical analysis on the mapped co-registered images; wherein displaying the trial image includes displaying an image that emphasizes pixels corresponding to structural or functional changes greater than a predetermined threshold change based on the statistical analysis.

10. The method of claim 9, wherein performing the statistical analysis includes determining a value representing the structural or functional change; and comparing the value with the predetermined threshold, wherein the displayed image only shows pixels with corresponding values that are greater than the predetermined threshold.

11. The method of claim 9, wherein performing the statistical analysis includes determining a value representing the structural or functional change; and comparing the value with the predetermined threshold, wherein the displayed image visually highlights pixels with corresponding values that are greater than the predetermined threshold.

12. The method of claim 9, wherein performing the statistical analysis includes comparing the trial image with an image generated with data obtained for a second subject receiving a placebo.

13. The method of claim 9, wherein performing the statistical analysis includes comparing the trial image with an image generated with data obtained for a second subject receiving a second treatment.

14. The method of claim 1, wherein the trial image is a surface projection onto a surface of the anatomical region.

15. The method of claim 1, further comprising determining an efficacy of the administered treatment based on the trial image.

16. A system, comprising:
computer memory storing instructions; and
a computer processor that executes the instructions stored in the computer memory, which causes the computer processor to:
obtain images generated from image data acquired at different times during a trial time period for a same anatomical region of a subject, wherein a treatment is administered to the subject for the trial;
co-register the images;
map the co-registered images to a reference image representing the anatomical region, and
generate a trial image of the anatomical region showing at least one of structural or functional physiological changes that occurred during the trial time period based on the mapped co-registered images.

17. The system of claim 16, wherein the instructions further cause the computer processor to:
perform a statistical analysis over the trial image and trial images for one or more other subjects receiving an alternative treatment or a placebo to assess efficacy of the treatment under trial.

18. The system of claim 16, wherein the instructions further cause the computer processor to:
select one of the images as a baseline image, wherein co-registering the images includes co-registering the images with the selected baseline image.

19. The system of claim 16, wherein the instructions further cause the computer processor to:
generate an average image based on the co-registered images; and
generate a transformation based on the average image; wherein mapping the co-registered images includes transforming the co-registered images with the generated transformation.

20. The system of claim 19, wherein the instructions further cause the computer processor to:
generate the transformation based on an anatomical model representing the region of interest.

21. The system of claim 20, wherein the transformation warps the co-registered images to fit the model.

22. The system of claim 20, wherein the anatomical model is a three dimensional volume.

23. The system of claim 16, wherein the instructions further cause the computer processor to:
select one of the co-registered images as a reference image; and
generate a transformation based on the reference image; wherein mapping the co-registered images includes transforming the co-registered images with the generated transformation.

24. A computer memory encoded with computer readable instructions, which, when executed by a computer processor, cause the computer processor to:
obtain images generated from image data acquired at different times during a trial time period for a same anatomical region of a subject, wherein a treatment is administered to the subject for the trial;
co-register the images;
map the co-registered images to a reference image representing the anatomical region wherein the reference image is not one of the obtained or co-registered images; and
generate a trial image of the anatomical region showing at least one of structural or functional physiological changes that occurred during the trial time period based on the mapped co-registered images.

25. The computer memory of claim 24, wherein the instructions further cause the computer processor to:

perform a statistical analysis over the trial image and trial images for one or more other subjects receiving an alternative treatment or a placebo to assess efficacy of the treatment under trial.

26. The computer memory of claim 24, wherein the instructions further cause the computer processor to:
select one of the images as a baseline image, wherein co-registering the images includes co-registering the images with the selected baseline image.

27. The computer memory of claim 24, wherein the instructions further cause the computer processor to:
generate an average image based on the co-registered images; and
generate a transformation based on the average image; wherein mapping the co-registered images includes transforming the co-registered images with the generated transformation.

28. The computer memory of claim 24, wherein the instructions further cause the computer processor to:
select one of the co-registered images as a reference image; and
generate a transformation based on the reference image; wherein mapping the co-registered images includes transforming the co-registered images with the generated transformation.

29. The computer memory of claim 28, wherein the instructions further cause the computer processor to:
generate the transformation based on an anatomical model representing the region of interest.

30. The computer memory of claim 29, wherein the anatomical model is a three dimensional volume.

* * * * *